(12) United States Patent
Campbell et al.

(10) Patent No.: US 10,687,525 B2
(45) Date of Patent: Jun. 23, 2020

(54) ENHANCEMENT OF CELL CRYOPRESERVATION WITH GLYCOLIPIDS

(71) Applicant: TISSUE TESTING TECHNOLOGIES LLC, North Charleston, SC (US)

(72) Inventors: Lia H. Campbell, Mount Pleasant, SC (US); Kelvin G M Brockbank, Charleston, SC (US)

(*) Notice: Subject to any disclaimer, the term of this patent is extended or adjusted under 35 U.S.C. 154(b) by 16 days.

(21) Appl. No.: 15/655,381

(22) Filed: Jul. 20, 2017

(65) Prior Publication Data

US 2018/0020658 A1 Jan. 25, 2018

Related U.S. Application Data

(60) Provisional application No. 62/365,512, filed on Jul. 22, 2016.

(51) Int. Cl.
*A01N 1/02* (2006.01)
*C07H 15/06* (2006.01)

(52) U.S. Cl.
CPC ......... *A01N 1/0221* (2013.01); *A01N 1/0252* (2013.01); *A01N 1/0284* (2013.01); *C07H 15/06* (2013.01)

(58) Field of Classification Search
None
See application file for complete search history.

(56) References Cited

U.S. PATENT DOCUMENTS

| | | | |
|---|---|---|---|
| 5,071,598 A | 12/1991 | Baldeschwieler et al. | |
| 5,242,792 A | 9/1993 | Rudolph et al. | |
| 5,629,145 A | 5/1997 | Meryman | |
| 5,648,206 A | 7/1997 | Goodrich, Jr. et al. | |
| 5,827,741 A | 10/1998 | Beattie et al. | |
| 5,955,448 A | 9/1999 | Colaco et al. | |
| 5,962,214 A | 10/1999 | Fahy et al. | |
| 6,127,177 A | 10/2000 | Toner et al. | |
| 6,187,529 B1 | 2/2001 | Fahy et al. | |
| 6,194,137 B1 | 2/2001 | Khirabadi et al. | |
| 6,274,303 B1 | 8/2001 | Wowk et al. | |
| 6,395,467 B1 | 5/2002 | Fahy et al. | |
| 6,596,531 B2 | 7/2003 | Campbell et al. | |
| 6,740,484 B1 | 5/2004 | Khirabadi et al. | |
| 8,604,002 B1* | 12/2013 | Walters | A61K 31/739 106/13 |
| 2002/0098470 A1 | 7/2002 | Toner et al. | |
| 2013/0146803 A1 | 6/2013 | Kawahara et al. | |

(Continued)

FOREIGN PATENT DOCUMENTS

WO 02/32225 A2 4/2002

OTHER PUBLICATIONS

Gibco, "Primary Human Keratinocytes", http://tools.thermofisher.com/content/sfs/manuals/3944%20primary%20keratinocytes.pdf, published Jan. 2005, accessed Mar. 19, 2019.*

(Continued)

*Primary Examiner* — Erin M. Bowers
(74) *Attorney, Agent, or Firm* — Oliff PLC

(57) ABSTRACT

Living cellular material may be preserved by incubating the cellular material in a culture medium containing at least one glycolipid, and then subjecting the cellular material to a preservation protocol.

7 Claims, 4 Drawing Sheets

(56) References Cited

U.S. PATENT DOCUMENTS

2015/0037783 A1* 2/2015 Herickhoff .......... A01N 1/0221
435/1.3
2016/0116454 A1 4/2016 Brockbank et al.

OTHER PUBLICATIONS

Sep. 29, 2017 International Search Report issued in Application No. PCT/US2017/043090.
Sep. 29, 2017 Written Opinion issued in Application No. PCT/US2017/043090.
Kent R. Walters, Jr., et al., "A nonprotein thermal hysteresis-producing xylomannan antifreeze in the freeze-tolerant Alaskan beetle Upis ceramboides," PNAS, vol. 106, No. 48, Dec. 1, 2009, pp. 20210-20215.
Kent R. Walters, Jr., "A thermal hysteresis-producing xylomannan glycolipid antifreeze associated with cold tolerance is found in diversa taxa," J. Comp Physiol B, (2011) 181:631-640.
Oct. 1, 2018 Preliminary Report on Patentability issued in International Application No. PCT/US2017/043090.
Jul. 11, 2018 Written Opinion issued in Application No. PCT/US2017/043090.

* cited by examiner

US 10,687,525 B2

ENHANCEMENT OF CELL CRYOPRESERVATION WITH GLYCOLIPIDS

CROSS-REFERENCE TO RELATED APPLICATION

This nonprovisional application claims the benefit of U.S. Provisional Application No. 62/365,512 filed Jul. 22, 2016. The disclosure of the prior application is hereby incorporated by reference in its entirety.

GOVERNMENT SUPPORT

This invention was made with government support under Grant Number: R43GM112176 awarded by the Department of Health and Human Services, National Institutes of Health, National Institute of General Medical Sciences. The government has certain rights in the invention

BACKGROUND

The present disclosure relates to the field of cell, tissue and organ preservation at low temperatures (e.g., cryopreservation). More specifically, the present disclosure relates to methods for treatment of cellular materials with glycolipids, such as, for example, antifreeze glycolipids (AFGLs) that have been isolated from freeze-tolerant/freeze-avoiding organisms and/or plants, and provides a cell population with enhanced cell survival post-preservation—even under suboptimal cooling conditions, such as rapid cooling.

Conventional approaches to cryopreservation generally include addition of 10% DMSO to cells in suspension in cryovials and slow rates of cooling, with or without induced nucleation, and storage at −80° C. or below −135° C. As long as viable cells are present upon thawing, cell yield is often a secondary consideration in conventional approaches. However, there are cell types and tissues that are difficult to preserve and situations where cell yield is critical such as for cell therapy applications. Alternative protocols and solutions that improve cell viability and yield (even under suboptimal cooling conditions) and allow for the preservation of cell types that are traditionally hard to preserve are needed.

Nature has developed a wide variety of alternative strategies for allowing organisms/plants to tolerate/survive extreme temperatures. The study of how organisms/plants survive extreme temperatures has revealed that they produce various antifreeze compounds, which help them either avoid freezing or tolerate freezing until warmer temperatures are available. For example, the discovery of antifreeze proteins in fish and insects has provided an avenue to explore alternative preservation strategies.

In this regard, it has been found that the presence of antifreeze proteins lowers the freezing point of the solution and also changes the shape and formation of ice. For example, anti-freeze peptides (AFPs) can adsorb to the surface of ice crystals, blocking the addition of water molecules to growth sites, which decreases the temperature at which the crystal grows (called the hysteretic freezing point) by as much as 13° C. AFPs can also bind to embryonic ice crystals, thereby inhibiting ice nucleation and permitting extensive supercooling well below the freezing point. They are also thought to be able to modify ice structure, inhibit recrystallization and modify the fluid properties of solutions, thereby extending survival of organisms in subzero environments. In this way, potentially less cryoprotectant may be used to preserve cells reducing potential cytotoxicity.

While anti-freeze peptides (AFPs) are known and have been studied extensively, various anti-freeze glycolipids (AFGLs) have also been found in several organisms/plants, including insects (both freeze tolerant insects and freeze avoiding insects), and freeze tolerant plants. However, prior to the methodology of the present disclosure, the use of such larger molecules in the context of preserving mammalian cells had been somewhat limited (in part because mammalian cell membranes are believed to be impermeable to larger molecules (Castro, A. G., Lapinski, J., Tunnacliffe, A. Nature Biotechnology 18:473, 2000) and it was previously believed that for molecules to be effective at enhancing survival, such molecules need to be present both on the inside and the outside of the cell membrane). The isolation of such AFGLs provides an opportunity to develop/enhance preservation methods for a variety of cell and tissue types.

SUMMARY OF THE INVENTION

This summary is provided to introduce a selection of concepts that are further described below in the detailed description. This summary is not intended to identify key or essential features of the claimed subject matter, nor is it intended to be used as an aid in limiting the scope of the claimed subject matter.

It was found that the incubation of cellular materials under various conditions in the presence of glycolipids, such as AFGLs isolated from one or more organisms, resulted in increased cell survival under various conditions, including, for example, suboptimal cooling conditions, such as rapid cooling.

The present application thus provides a method for treatment of cellular materials with glycolipids, such as AFGLs, that enhances the ability of these cellular materials to survive a cryopreservation procedure, even under suboptimal cooling conditions, such as rapid cooling.

DETAILED DESCRIPTION

Terminology and Definitions

Figure 1:
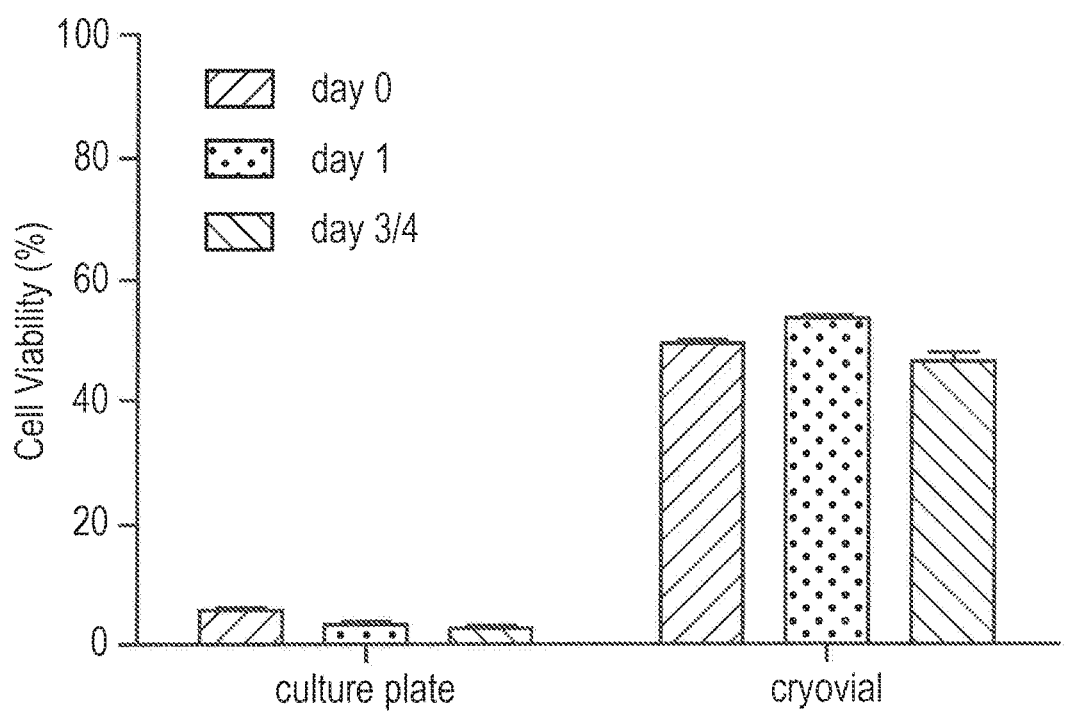
FIG. 1 is an illustration of the data obtained with respect to cell viability after cryopreservation where keratinocytes were cryopreserved in vials or in culture plates in 10% DMSO in RPMI.

In the following description, numerous details are set forth to provide an understanding of the present disclosure. However, it may be understood by those skilled in the art that the methods of the present disclosure may be practiced without these details and that numerous variations or modifications from the described embodiments may be possible.

At the outset, it should be noted that in the development of any such actual embodiment, numerous implementation—specific decisions may be made to achieve the developer's specific goals, such as compliance with system related and business related constraints, which will vary from one implementation to another. Moreover, it will be appreciated that such a development effort might be complex and time consuming but would nevertheless be a routine undertaking for those of ordinary skill in the art having the benefit of this disclosure. In addition, the composition used/disclosed herein can also comprise some components other than those cited. In the summary and this detailed description, each numerical value should be read once as modified by the term "about" (unless already expressly so modified), and then read again as not so modified unless otherwise indicated in context.

As used herein, the term "about" used in connection with a quantity is inclusive of the stated value and has the meaning dictated by the context. For example, it includes at least the degree of error associated with the measurement of the particular quantity. When used in the context of a range, the modifier "about" should also be considered as disclosing the range defined by the absolute values of the two endpoints. For example, the range "from about 2 to about 4" also discloses the range "from 2 to 4."

Unless otherwise expressly stated herein, the modifier "about" with respect temperatures (° C.) refers to the stated temperature or range of temperatures, as well as the stated temperature or range of temperatures +/−1-4% (of the stated temperature or endpoints of a range of temperatures) of the stated. Regarding cell viability and cell retention (%), unless otherwise expressly stated herein, the modifier "about" with respect to cell viability and cell retention (%) refers to the stated value or range of values as well as the stated value or range of values +/−1-3%. Regarding expression contents, such as, for example, with the units in either parts per million (ppm) or parts per billion (ppb), unless otherwise expressly stated herein, the modifier "about" with respect to cell viability and cell retention (%) refers to the stated value or range of values as well as the stated value or range of values +/−1-3%. Regarding expressing contents with the units μg/mL, unless otherwise expressly stated herein, the modifier "about" with respect to value in μg/mL refers to the stated value or range of values as well as the stated value or range of values +/−1-4%. Regarding molarity (M), unless otherwise expressly stated herein, the modifier "about" with respect to molarity (M) refers to the stated value or range of values as well as the stated value or range of values +/−1-2%. Regarding, cooling rates (° C./min), unless otherwise expressly stated herein, the modifier "about" with respect to cooling rates (° C./min) refers to the stated value or range of values as well as the stated value or range of values +/−1-3%.

Also, in the summary and this detailed description, it should be understood that a range listed or described as being useful, suitable, or the like, is intended to include support for any conceivable sub-range within the range at least because every point within the range, including the end points, is to be considered as having been stated. For example, "a range of from 1 to 10" is to be read as indicating each possible number along the continuum between about 1 and about 10. Additionally, for example, +/−1-4% is to be read as indicating each possible number along the continuum between 1 and 4. Furthermore, one or more of the data points in the present examples may be combined together, or may be combined with one of the data points in the specification to create a range, and thus include each possible value or number within this range. Thus, (1) even if numerous specific data points within the range are explicitly identified, (2) even if reference is made to a few specific data points within the range, or (3) even when no data points within the range are explicitly identified, it is to be understood (i) that the inventors appreciate and understand that any conceivable data point within the range is to be considered to have been specified, and (ii) that the inventors possessed knowledge of the entire range, each conceivable sub-range within the range, and each conceivable point within the range. Furthermore, the subject matter of this application illustratively disclosed herein suitably may be practiced in the absence of any element(s) that are not specifically disclosed herein.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of concepts according to the disclosure. This description should be read to include one or at least one and the singular also includes the plural unless otherwise stated.

The terminology and phraseology used herein is for descriptive purposes and should not be construed as limiting in scope. Language such as "including," "comprising," "having," "containing," or "involving," and variations thereof, is intended to be broad and encompass the subject matter listed thereafter, equivalents, and additional subject matter not recited.

Also, as used herein any references to "one embodiment" or "an embodiment" means that a particular element, feature, structure, or characteristic described in connection with the embodiment is included in at least one embodiment. The appearances of the phrase "in one embodiment" in various places in the specification are not necessarily referring to the same embodiment.

As used herein, the term "room temperature" refers to a temperature of about 18° C. to about 25° C. at standard pressure. In various examples, room temperature may be about 18° C., about 19° C., about 20° C., about 21° C., about 22° C., about 23° C., about 24° C., or about 25° C.

As used herein, "cellular material" or "cellular sample" refers to living biological material containing cellular components, whether the material is natural or man-made and includes cells, tissues and organs, whether natural or man-made. Such terms also mean any kind of living material to be cryopreserved, such as cells, tissues and organs. In some embodiments, the cells, tissues and organs may be mammalian organs (such as human organs), mammalian cells (such as human cells) and mammalian tissues (such as human tissues).

As used herein, the term "organ" refers to any organ, such as, for example, liver, lung, kidney, intestine, heart, pancreas, testes, placenta, thymus, adrenal gland, arteries, veins, lymph nodes, bone or skeletal muscle. As used herein, the term "tissue" or "tissues" comprises any tissue type comprising any kind of cell type (such as from one of the above-mentioned organs) and combinations thereof, including, for example, ovarian tissue, testicular tissue, umbilical cord tissue, placental tissue, connective tissue, cardiac tissue, tissues from muscle, cartilage and bone, endocrine tissue, and neural tissue. The term "tissue" or "tissues" may also comprise adipose tissue or dental pulp tissue. In some embodiments, the tissue or organ is a obtained from a human such as a human liver, human lung, human kidney, human intestine, human heart, human pancreas, human testes, human placenta, human thymus, human adrenal gland, human arteries, human veins, human lymph nodes, human bone or human skeletal muscle.

As used herein, the term "cell(s)" comprises any type of cells, such as, for example, somatic cells (including all kind of cells in tissue or organs), fibroblasts, keratinocytes, hepatocytes, cardiac myocytes, smooth muscle cells, stem cells, progenitor cells, oocytes, spermatozoa, and germ cells. Such cells may be in isolated form or in a not isolated form such as in the form of a cell-containing bodily fluid, a tissue or organ. In some embodiments, the cells are from a mammal tissue or organ, such as a human tissue or organ described above.

As used herein, "preservation protocol" refers to a process for provision of shelf life to a cell containing, living biological material. Preservation protocols may include cryopreservation by freezing and/or vitrification and/or anhydrobiotic preservation by either freeze-drying or desiccation.

As used herein, the term "cryoprotectant" means a chemical that minimizes ice crystal formation in a cell/tissue/organ when the tissue is cooled to subzero temperatures and results in substantially no damage to the cell/tissue/organ after warming, in comparison to the effect of cooling without cryoprotectant.

As used herein, the term "functional after cryopreservation" in relation to a cryopreserved material means that the cryopreserved material, such as organs, tissue or cells, after cryopreservation retains an acceptable and/or intended function after cryopreservation. In some embodiments, the cellular material after cryopreservation retains all its indented function.

In some embodiments, the cellular cryopreserved material preserved by the methods of the present disclosure retains at least 50% of the intended function, such as at least 60% of the intended function, such as at least 70% of the intended function, such as at least 80% of the intended function, such as at least 90% of the intended function, such as at least 95% of the intended function, such as 100% of the intended function. For example, along with preserving the viability of the cells, it may be important to also maintain/preserve the physiological function of the cell/tissue/organ, e.g. for a heart the pumping function, and/or the ability of a tissue/cell(s) (e.g., those to be transplanted) to integrate with surrounding tissue/cell(s).

As used herein, the term "glycolipid" refers to any molecule with at least one carbohydrate chain linked to a fatty acid chain, a ceramide, or any other lipid. Glycolipids, such as AFGLs, may be of natural (e.g., isolated and/or purified) or synthetic origin. The term "carbohydrate chain" refers to a sugar moiety containing more than one monosaccharide unit. That is, the term carbohydrate includes polysaccharides and/or oligosaccharides. In embodiments, the carbohydrate may also be a mixture of various monosaccharide repeating units, such as, for example, a polysaccharide including xylose and mannose repeating units. The term "lipid" as used herein, refers to any molecule from a group of naturally occurring or synthetic molecules that include fats, waxes, sterols, fat-soluble vitamins, monoglycerides, diglycerides, triglycerides, phospholipids, and the like.

The term "isolated" as used herein, refers to any composition or mixture that has undergone a laboratory purification procedure including, for example, extraction, centrifugation, ice-affinity purification (e.g., with multiple freeze/thaw ice purification cycles) and/or chromatographic separation (e.g., thin layer chromatography or high performance liquid chromatography). Usually such procedures provide an isolated composition or mixture based upon physical, chemical, or electrical potential properties. Depending upon the choice of procedure an isolated composition or mixture may contain other compositions, compounds or mixtures having similar chemical properties.

As used herein, the term "purified" refers to molecules (e.g., glycolipids) that are removed from their natural environment, isolated or separated. For example, in some embodiments, the glycolipids that are used in the methods of the present disclosure are purified glycolipids (such as AFGLs isolated from one or more organism/plant) that are free from other components (i.e., detectable spectroscopic signals (e.g., $^1$H NMR signals acquired with a Varian UNITY Plus 600 MHz FT-NMR spectrometer) of the other components are absent) from the with which they are naturally associated (such as, for example, proteins (such as AFPs)).

As used herein, "substantially purified" molecules (e.g., substantially purified glycolipids) are at least 50% free, or at least 90% free, or at least 95%, or at least 99% free from other components with which they are naturally associated. For example, in some embodiments, the glycolipids that are used in the methods of the present disclosure are substantially purified glycolipids (such as AFGLs isolated from one or more organism/plant) that are at least 50% free, or at least 90% free, or at least 95%, or at least 99% free from other components with which they are naturally associated (such as, for example, proteins (such as AFPs)).

As used herein, the term "sterile" means free from living germs, microorganisms and other organisms capable of proliferation.

As used herein, the term "substantially free of cryoprotectant" means a cryoprotectant in an amount less than 0.01 w/w %. In some embodiments, the methods of the present disclosure may use and/or achieve a medium/solution and/or cellular material that is substantially free of cryoprotectant, such as DMSO.

Embodiments

The present disclosure is directed to methods for preserving living materials/samples/organ(s)/tissue(s)/cell(s) (The terms "materials," "samples,", "organ(s)", "tissue(s)" and "cell(s)" are used interchangeably and encompass any living biological material containing cellular components).

The methods of the present disclosure comprise bringing cells into contact with a solution containing at least one glycolipid (and optionally a cryoprotectant). In some embodiments, this may comprise incubating cells in a medium/solution containing at least one glycolipid (and optionally a cryoprotectant), such as incubating (or bringing into contact) cells in a medium containing at least one glycolipid (and optionally a cryoprotectant). In embodiments, the at least one glycolipid may be present in the medium/solution in an amount effective to provide an environment more conducive to survival of the cells (even for hard to preserve cells, like keratinocytes, hepatocytes, and cardiac myocytes).

In the methods of the present disclosure, the cells are protected during cryopreservation after being brought into contact with the at least one glycolipid (and optionally a cryoprotectant), which occurs prior to cooling the cells to the cryopreservation temperature. In embodiments, being brought into contact with the at least one glycolipid (and optionally a cryoprotectant) means that the cells are made to be in contact in some manner with the at least one glycolipid (and optionally a cryoprotectant) such that during the reduction of temperature to the cryopreservation temperature the viability of the cells does not significantly deteriorate because the cells have been stabilized/protected by the at least one glycolipid (and optionally a cryoprotectant) in the cryopreservation composition.

The glycolipids suitable for use in the methods of the present disclosure may include any glycolipid, such as the AFGLs described in U.S. Pat. No. 8,604,002, the disclosure of which is hereby incorporated by reference in its entirety, that has a structure that inhibits/decreases/prevents ice formation. In this regard, suitable glycolipids, such as AFGLs, may have a structure that prevents the lethal spread of extracellular ice into the cytoplasm. In some embodiments, suitable glycolipids, such as the AFGLs, may have a structure that such that it is a thermal hysteresis (TH)-producing glycolipid, such as an glycolipid that able to be positioned relative to the living cellular material (e.g., on the outer surface of the cell membrane) being cryopreserved in a manner that prevents the lethal spread of extracellular ice into the cytosol. In some embodiments, this orientation may place an ice-binding motif on the cell surface. Suitable glycolipids (that accomplish the above mentioned functions) may include, for example, xylomannan-based antifreeze glycolipids, such as glycolipids in which mannose and xylose are the major saccharide components (with variable amounts of lipid, such as a fatty acid), which are described in U.S. Pat. No. 8,604,002.

The isolation/production of AFGLs is described in U.S. Pat. No. 8,604,002. Briefly, AFGLs may be isolated and purified from natural sources using membrane extraction followed by ice binding methods, or they can be synthesized by chemical and/or enzymatic procedures. Plants that naturally produce the AFGLs, especially perennials, such as *Solanum dulcamara* (bittersweet nightshade), are favorable sources of these materials. Such plants can be grown as a field of crops, harvested at the appropriate time in the autumn after the AFGLs have been produced, and the AFGLs can then be extracted and purified for use in various antifreeze applications.

Thermal hysteresis (TH), a difference between the melting and freezing points of a solution that is indicative of the presence of large molecular mass antifreezes (e.g., antifreeze proteins), has been described in animals, plants, bacteria and fungi. A highly active thermal hysteresis factors (THFs) from the freeze-tolerant beetle, *Upis ceramboides*, has been isolated by means of ice affinity. Amino acid chromatographic analysis, polyacrylamide gel electrophoresis. UV-Vis spectrophotometry and NMR spectroscopy indicated that the THF contains little or no protein, yet it produced 3.7±0.3° C. of TH at 5 mg/mL, comparable to that of the most active insect antifreeze proteins. Compositional and structural analyses show that this antifreeze contains a β-mannopyranosyl-(1→4) β-xylopyranose backbone and a fatty acid component, where the lipid can be covalently linked to the saccharide or electrostatically (ionically) bound to the saccharide.

In some embodiments, the glycolipid used in the methods of the present disclosure may have little or no proteins associated with them, and possess significant thermal hysteresis properties. For example, the glycolipid used in the methods of the present disclosure may include an antifreeze glycolipid composition comprising a polysaccharide moiety of:

where D-Manp represents a D-mannopyranose moiety, D-Xylp represents a D-xylopyranose moiety, and n is about 5 to about 70; and one or more lipid moieties covalently linked to the polysaccharide moiety of the above formula or electrostatically associated with the polysaccharide moiety shown above.

The glycolipid used in the methods of the present disclosure may be a collection of the glycolipid conjugates, or can be a collection of the xylomannan polysaccharide electrostatically associated with lipid moieties, such as fatty acids, for example, through ionic bonding. For example, the methods of the present disclosure may include one or more glycolipid of the following formulas:

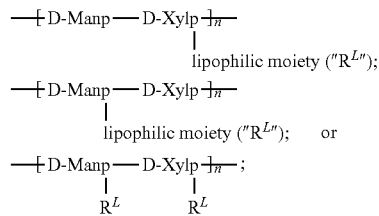

where the lipophilic moiety ($R^L$) is covalently bonded to one of the saccharide components, both, or a combination thereof; the lipid moiety ($R^L$) can be covalently bonded to a saccharide moiety directly (e.g., through an ether or ester group) or it can be bonded to the saccharide moiety through a linking group, such as glycerol.

In some embodiments, the glycolipid used in the methods of the present disclosure may be a xylomannan polysaccharide that may be electrostatically associated with lipid moieties, as represented by the following formula:

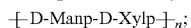

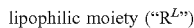

where the lipophilic moiety is, for example, an alkyl chain substituted with one or more hydroxyl groups or carboxy groups, a fatty acid, a mono-, di-, or tri-glyceride, a sterol, or a phospholipid.

In some embodiments, the lipophilic moiety $R^L$ may be any lipid molecule or moiety associated with the saccharide chain, by electrostatic interactions or by direct covalent bonding. The lipid molecule can be, for example, an alkyl chain, a fatty acid, a mono-, di-, or tri-glyceride, a sterol, or a phospholipid. When the lipid molecule is covalently bonded to the saccharide chain, the covalent bonding can be at any hydroxyl group of the saccharide chain (e.g., at C2, C3, C4 when not linked to another sugar moiety, C6, or the anomeric position C1). The conjugation can be present on one or more mannose saccharides, one or more xylose saccharides, or a combination thereof.

In some embodiments, the glycolipid used in the methods of the present disclosure may include a polysaccharide moiety as follows:

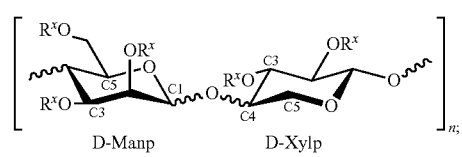

where n is about 5 to about 70, and each Rx can independently be H or a lipophilic moiety $R^L$, where at least one Rx of the molecule is $R^L$. When the composition is an electrostatic association of the xylomannan and the lipid moiety, the xylomannan can be a saccharide of the following formula:

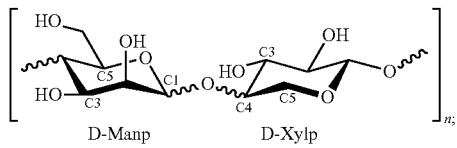

where a lipid moiety is electrostatically associated to one or more of the oxygen atoms of the saccharide of the above formula. In some embodiments, the glycolipid used in the methods of the present disclosure may be combinations of the various known AFGLs, such as those described in U.S. Pat. No. 8,604,002, such as a combination of a polysaccharide of Formula VI and a polysaccharide of Formula VII of U.S. Pat. No. 8,604,002, where some lipid moieties are covalently bonded to the polysaccharide and others are ionically associated to the polysaccharide of Formula VI and/or Formula VII of U.S. Pat. No. 8,604,002.

In some embodiments, in the methods of the present disclosure an aqueous medium (the terms "medium" and "solution" are used interchangeably) containing the at least one glycolipid (and optionally a cryoprotectant) may be combined with cells to prepare a cryopreservation composition comprising a cell suspension. The aqueous medium can contain any suitable concentration of the at least one glycolipid (and optionally a cryoprotectant) for these purposes.

In some embodiments, at least one glycolipid is used in an amount in the methods of the present disclosure such that it results in an improved viability (post-cryopreservation) of the living cellular material/sample selected from the group consisting of organs, cells and tissues, such as mammalian organs, mammalian cells, and mammalian tissues (including those which may be subsequently transplanted). The phrases, "improved cell viability" or "improved viability," refer, for example, to a cell viability (%) of at least 60%, such as 80% or more. The improved cell viability (%) may be 50% or more, 60% or more, 70% or more, 73% or more, 75% or more, 77% or more, 80% or more, 83% or more, 85% or more, 87% or more, 90% or more, 93% or more, 95% or more, 97% or more, 98% or more, or 99% or more.

In some embodiments, at least one glycolipid is used in an amount in the methods of the present disclosure such that it is effective to accomplish one or more of the following: produce thermal hysteresis, inhibit ice nucleation, modify ice structure, decrease ice formation, prevent ice formation, decrease/prevent ice formation to an extent that would allow the use of more rapid cooling rates, decrease/prevent ice formation to an extent that would allow a reduction in the amount of cryoprotectant required providing an environment more conducive to cell survival for hard to preserve cells and tissues.

In some embodiments, the at least one glycolipid represents from about 0.000001% to about 0.5% of the total weight of the medium comprising the cells to be preserved, such as from about 0.00001% to about 0.1% of the total weight of the total weight of the medium comprising the cells to be preserved, or from about 0.0005% to about 0.05% of the total weight of the medium comprising the cells to be preserved.

In some embodiments, the at least one glycolipid may be present in any desired/effective amount to accomplish the intended outcome. In some embodiments, at least one glycolipid may be present in the medium in an amount greater than about 0.01 pg/ml, such as in an amount greater than about 0.1 pg/ml, or in an amount greater than about 1 pg/ml, or in an amount greater than about 10 pg/ml, or in an amount greater than in an amount greater than about 200 pg/ml. In some embodiments, the at least one glycolipid is present in the medium in an amount greater than about 0.01 ng/ml, such as in an amount greater than about 0.1 ng/ml, or in an amount greater than about 1 ng/ml, or in an amount greater than about 10 ng/ml, or in an amount greater than in an amount greater than about 200 ng/ml. In some embodiments, the at least one glycolipid is present in the medium in an amount greater than about 0.01 µg/ml, such as in an amount greater than about 0.1 µg/ml, or in an amount greater than about 1 µg/ml, or in an amount greater than about 10 µg/ml, or in an amount greater than in an amount greater than about 200 µg/ml.

In some embodiments, the medium contains the at least one glycolipid at a concentration ranging from 1 pM to 1000 µM, from 1 pM to 500 µM, from 1 pM to 30 µM, from 1 pM to 1000 nM, from 1 pM to 500 nM, from 1 pM to 250 nM, from 100 pM to 750 µM, from 100 pM to 500 µM, from 100 pM to 20 µM, from 100 pM to 1000 nM, from 1 pM to 750 nM, from 1 pM to 500 nM, from 1 pM to 250 nM, from 1 pM to 1 nM, from 500 pM to 500 µM, from 500 pM to 250 µM, from 500 pM to 100 µM, from 500 pM to 10 µM, from 500 pM to 1000 nM, from 500 pM to 750 nM, from 500 pM to 500 nM, from 500 pM to 250 nM, from 500 pM to 100 nM, from 500 pM to 1 nM, from 1 nM to 1000 µM, from 1 nM to 750 µM, from 1 nM to 500 µM, from 1 nM to 250 µM, from 1 nM to 100 µM, from 1 pM to 1 µM, from 100 nM to 1000 µM, from 100 nM to 750 µM, from 100 nM to 500 µM, from 100 nM to 250 µM, from 100 nM to 100 µM, from 100 pM to 1 µM, from 250 nM to 1000 µM, from 250 nM to 750 µM, from 250 nM to 500 µM, from 250 nM to 250 µM, from 250 nM to 100 µM, from 250 nM to 1 µM, from 500 nM to 1000 µM, from 500 nM to 750 µM, 500 nM to 500 µM, from 500 nM to 250 µM, from 100 nM to 100 µM, from 500 nM to 1 µM, from 750 nM to 1000 µM, from 750 nM to 750 µM, from 750 nM to 500 µM, from 750 nM to 250 µM, from 750 nM to 100 µM, from 750 nM to 1 µM, from 0.5 µM to 1000 µM, from 10 µM to 950 µM, from 20 µM to 900 µM, from 30 µM to 850 µM, from 40 µM to 800 µM, from 50 µM to 750 µM, from 60 µM to 700 µM, from 70 µM to 650 µM, from 80 µM to 600 µM, from 90 µM to 550 µM, from 100 µM to 500 µM, from 110 µM to 450 µM, from 120 µM, to 400 µM, from 130 µM to 350 µM, from 140 µM to 300 µM, from 150 µM to 250 µM, from 160 µM to 200 µM, from 0.5 µM to 100 µM, from 1 µM to 90 µM, from 5 µM to 90 µM, from 10 µM to 85 µM, from 10 µM to 75 µM, from 20 µM to 85 µM, from 20 µM to 65 µM, from 30 µM to 70 µM, from 30 to 50 µM, from 40 µM to 80 µM, or from 40 µM to 50 µM, wherein any concentration occurring within the above ranges can also serve as an endpoint for a range.

In some embodiments, the medium contains the at least one glycolipid at a concentration ranging from 0.001 ppb to 10,000 ppm, from 0.01 ppb to 1,000 ppm, from 0.1 ppm to 100 ppm, from 1 ppb to 100 ppm, from 1 ppm to 500 ppm, from 1 ppb to 250 ppm, 100 ppm to 750 ppm, from 100 ppm to 500 ppm, from 100 ppm to 1000 ppm, from 1 ppm to 750 ppm, from 0.1 ppm to 500 ppm, from 1 ppb to 250 ppm, from 1 ppb to 1 ppm, from 500 ppb to 500 ppm, from 500 ppb to 250 ppm, from 500 ppb to 100 ppm, from 500 ppb to 10 ppm, from 500 ppb to 1000 ppm, from 500 ppb to 750 ppm, from 500 ppb to 500 ppm, from 50 ppb to 250 ppm, from 1 ppm to 1000 ppm, from 1 ppm to 750 ppm, from 1 ppm to 500 ppm, from 1 ppm to 250 ppm, from 1 ppm to 100 ppm, from 1 ppm to 1,000 ppm, from 100 ppm to 1,000 ppm, from 100 ppm to 750 ppm, from 100 ppm to 500 ppm, from 100 ppm to 250 ppm, from 10 ppm to 950 ppm, from 20 ppm to 900 ppm, from 30 ppm to 850 ppm, from 40 ppm to 800 ppm, from 50 ppm to 750 ppm, from 60 ppm to 700 ppm, from 70 ppm to 650 ppm, from 80 ppm to 600 ppm, from 90 ppm to 550 ppm, from 100 ppm to 500 ppm, from 110 ppm to 450 ppm, from 120 ppm, to 400 ppm, from 130 ppm to 350 ppm, from 140 ppm to 300 ppm, from 150 ppm to 250 ppm, from 160 ppm to 200 ppm, from 0.5 ppm to 100 ppm, from 1 ppm to 90 ppm, from 5 ppm to 90 ppm, from 5 ppm to 85 ppm, from 5 ppm to 75 ppm, from 2 ppm to 15 ppm, from 2 ppm to 50 ppm, from 3 ppm to 20 ppm, from 3 to 50 ppm, from 4 ppm to 80 ppm, or from 4 ppm to 50 ppm, wherein any concentration occurring within the above ranges can also serve as an endpoint for a range.

In embodiments, the above mediums comprising the at least one glycolipid may be contacted with the cells or tissues for any desired duration, such as until a desired dosage (such as an effective dosage) of the at least one glycolipid is present on the cells or tissues to afford in an improved viability (post-cryopreservation), and/or to prevent/protect against tissue damage and/or to accomplish one or more of the following: produce thermal hysteresis, inhibit ice nucleation, modify ice structure, decrease ice formation, prevent ice formation, decrease/prevent ice formation to an extent that would allow the use of more rapid cooling rates, decrease/prevent ice formation to an extent that would allow a reduction in the amount of cryoprotectant required to provide an environment more conducive to cell survival for hard to preserve cells and tissues.

In some embodiments, the cells to be cryopreserved may also be in contact with a freezing-compatible pH buffer comprised of, for example, at least a basic salt solution, an energy source (for example, glucose), and a buffer capable of maintaining a neutral pH at cooled temperatures. Well known such materials include, for example, Dulbecco's Modified Eagle Medium (DMEM). This material may also be included as part of the cryopreservation composition. See, e.g., Campbell et al., "Cryopreservation of Adherent Smooth Muscle and Endothelial Cells with Disaccharides," In: Katkov I. (ed.) Current Frontiers in Cryopreservation. Croatia: In Tech (2012); and Campbell et al., "Development of Pancreas Storage Solutions: Initial Screening of Cytoprotective Supplements for β-cell Survival and Metabolic Status after Hypothermic Storage," Biopreservation and Biobanking 11(1): 12-18 (2013).

The cryopreservation composition to be used in the methods of the present disclosure may also comprise any cryoprotective materials known in the art. In some embodiments, The cryoprotectant compounds may be present in the cryopreservation composition in an amount of from, for example, about 0.05 M to about 11 M, about 0.1 to about 8 M, about 0.25 to about 11 M, about 1 to about 11 M, about 2 to about 11 M, about 4 to about 11 M, about 6 to about 11 M, about 8 to about 11 M, about 0.25 to about 11 M, about 0.25 to about 9 M, about 0.25 to about 8 M, about 0.25 to about 7 M, about 0.25 to about 10 M, about 1 to about 7 M, about 1 to about 8 M, about 1 to about 9 M, about 3 to about 10 M, about 2 to about 10 M, about 0.5 to about 10 M, about 0.5 to about 9 M, about 0.5 to about 9 M, about 0.5 to about 8 M, or about 0.5 to about 7 M, or about 6.5 to about 11 M. In some embodiments, the cryoprotectant compounds may be present in the cryopreservation composition in an amount of from, for example, about 0.05 M to about 6 M, about 0.1 to about 3 M, about 0.25 to about 6 M, about 1 to about 6 M, about 2 to about 6 M, about 3 to about 6 M, about 4 to about 6 M, about 5 to about 6M, about 0.25 to about 1 M, about 0.25 to about 2 M, about 0.25 to about 3 M, about 0.25 to about 4 M, about 0.25 to about 5 M, about 1 to about 4 M, about 1 to about 3 M, about 1 to about 2 M, about 3 to about 5 M, about 2 to about 4 M, about 0.5 to about 6 M, about 0.5 to about 5 M, about 0.5 to about 4 M, about 0.5 to about 3 M, about 0.5 to about 2 M, or about 0.5 to about 1M.

In some embodiments, the cells to be preserved the cells to be preserved may be brought into contact with a cryoprotectant-containing composition before, during or after incubating the cells to be preserved in a medium containing at least one glycolipid.

Suitable cryoprotectants may include, for example, acetamide, agarose, alginate, alanine, albumin, ammonium acetate, anti-freeze proteins, butanediols (such as 2,3-butanediol), chondroitin sulfate, chloroform, choline, cyclohexanediols, cyclohexanediones, cyclohexanetriols, dextrans, diethylene glycol, dimethyl acetamide, dimethyl formamide (such as n-dimethyl formamide), dimethyl sulfoxide, erythritol, ethanol, ethylene glycol, ethylene glycol monomethyl ether, formamide, glucose, glycerol, glycerophosphate, glyceryl monoacetate, glycine, glycoproteins, hydroxyethyl starch, inositol, lactose, magnesium chloride, magnesium sulfate, maltose, mannitol, mannose, methanol, methoxy propanediol, methyl acetamide, methyl formamide, methyl ureas, methyl glucose, methyl glycerol, phenol, pluronic polyols, polyethylene glycol, polyvinylpyrrolidone, proline, propanediols (such as 1,2-propanediol and 1,3-propanediol), pyridine N-oxide, raffinose, ribose, serine, sodium bromide, sodium chloride, sodium iodide, sodium nitrate, sodium nitrite, sodium sulfate, sorbitol, sucrose, trehalose, triethylene glycol, trimethylamine acetate, urea, valine and xylose. Other cryoprotectants that may be used in the present disclosure are described in U.S. Pat. No. 6,395, 467 to Fahy et al.; U.S. Pat. No. 6,274,303 to Wowk et al.; U.S. Pat. No. 6,194,137 to Khirabadi et al.; U.S. Pat. No. 6,187,529 to Fahy et al.; U.S. Pat. No. 5,962,214 to Fahy et al., U.S. Pat. No. 5,955,448 to Calaco et al.; U.S. Pat. No. 5,629,145 to Meryman; and/or WO 02/32225 A2, which corresponds to U.S. patent application Ser. No. 09/691,197 to Khirabadi et al., the disclosures of which are each hereby incorporated by reference in their entireties.

In some embodiments of the present disclosure, the cryoprotectant-containing composition may contain at least one glycolipid and at least one sugar. The sugar may be a mixture of sugars and may contain at least one polysaccharide, a disaccharide, such as trehalose and/or sucrose, and/or a trisaccharide, such as raffinose. The composition may contain from about 0.1 to 2.0M sugar, or from about 0.2 to 0.6M sugar. The cryoprotectant-containing composition may be a glycolipid-containing medium. Optionally, additional sugars and/or other cryoprotectants may be added to this culture medium prior to freezing or vitrifying the cellular material.

The cryoprotectant composition may also include at least one cyclohexanediol (CHD) compound, for example the cis or trans forms of 1,3-cyclohexanediol (1,3CHD) or 1,4-cyclohexanediol (1,4CHD), or racemic mixtures thereof, as a cryoprotectant compound.

The CHD compound may be present in the cryopreservation composition in an amount of from, for example, about 0.05 to about 2 M, about 0.1 M to about 1 M, about 0.1 to about 2 M, about 0.1 to about 1 M, about 0.1 to about 1.5 M, about 0.1 to about 0.5 M, about 0.1 to about 0.25 M, about 1 to about 2 M, about 1.5 to about 2 M, about 0.75 to about 2 M, about 0.75 to about 1.5 M, about 0.75 to about 1 M, about 0.05 to about 1 M, about 0.05 to about 0.75 M, about 0.05 to about 0.5 M, or about 0.05 to about 0.1 M. The cryopreservation composition also may include a solution well suited for organ storage of cells, tissues and organs. The solution may include the buffers discussed above. The solution may be, for example, the EuroCollins Solution, which is composed of dextrose, potassium phosphate monobasic and dibasic, sodium bicarbonate, and potassium chloride. See, e.g., Taylor et al., "Comparison of Unisol with Euro-Collins Solution as a Vehicle Solution for Cryoprotectants," Transplantation Proceedings 33: 677-679 (2001).

Still further, the cryopreservation composition for use in the methods of the present disclosure may also include an anti-freeze protein/peptide (AFP), or "thermal hysteresis" proteins, (THPs). Naturally occurring AFPs are believed to be able to bind to the prism face of developing ice crystals, thereby altering their formation. Any newly discovered or well-known AFPs may be used in the present method in this regard. See, e.g., Sicheri and Yang, Nature, 375:427-431, (1995), describing eight such proteins; DeVries, "Antifreeze glycopeptides and peptides: interactions with ice and water," Meth. Enzymol. 127:293-303 (1986); Duman, "Antifreeze and ice nucleator proteins in terrestrial arthropods," Annual Rev. Physiol. 63:327-3257 (2001); Holmstrup et al. "Dehydration and cold hardiness in the Arctic collembolan *Onychiurus arcticus*," J. Comp. Physiol. B 168: 197-203 (1998); Kuiper et al., "Purification of antifreeze proteins by adsorption to ice," Biochem. Biophys. Res. Commun. 300(3): 64-68 (2003); Miller, "Cold-hardiness strategies of some adult and immature insects overwintering in interior Alaska," Comp. Biochem. Physiol. 73A: 595-604 (1982); Neven et al., "Purification and characterization of an insect hemolymph lipoprotein ice nucleator: evidence for the importance of phosphatidylinositol and apolipoprotein in the ice nucleator activity," J. Comp. Physiol. B 159: 71-82 (1989); Sformo et al., "Deep supercooling, vitrification and limited survival to −100° C. in the Alaskan beetle *Cucujus clavipes puniceus* larvae," J. Exp. Biol. 213(3): 502-509 (2010); Storey et al., "Freeze tolerance in animals," Physiol. Rev. 68: 27-84 (1988); Storey et al., "Biochemical adaptation for cold hardiness in insects," Phil. Trans. R. Soc. Lond. B326: 635-54 (1990); Walters et al., "Freeze tolerance in the Arctic Alaska Stonefly, Nemoura arctica," J. Exp. Biol. 212: 305-12 (2009a); Walters et al., "Cryoprotectant biosynthesis and the selective accumulation of threitol in the freeze tolerant Alaskan beetle, *Upis ceramboides*," J. Biol. Chem. 284: 16822-16831 (2009b); Exemplary AFPs include AFPI (AFP type I), AFPIII (AFP type III) and/or AFGP, the disclosures of which are each hereby incorporated by reference in their entireties. The AFP may be present in the cryopreservation composition in an amount of from, for example, about 0.001 to about 1 mg/mL, about 0.05 to about 0.5 mg/mL, or about 0.1 to about 0.75 mg/mL of composition, for each AFP present.

In some embodiments, the at least one glycolipid may act as a replacement for a cryoprotectant, such as, for example, DMSO, or as a supplement to such other cryoprotectants to reduce the concentration thereof, such as to non-toxic concentrations, at which the cryoprotectant achieves the same or better protective effects with regard to preserving as much functionality of the cryopreserved material/sample during the cryopreservation procedure. In some embodiments, at least one glycolipid is used in an amount in the methods of the present disclosure such that it is effective to act as a cryoprotectant for a living material/sample selected from the group consisting of organs, cells and tissues, such as mammalian organs, mammalian cells, and mammalian tissues (including those which may be subsequently transplanted).

The cells that may be used in the methods of the present disclosure can be any suitable cell composition. In some embodiments, the cells can be skin cells, keratinocytes, skeletal muscle cells, cardiac muscle cells, lung cells, mesentery cells, adipose cells, stem cells, hepatocytes, epithelial cells, Kupffer cells, fibroblasts, neurons, cardio myocytes, myocytes, chondrocytes, pancreatic acinar cells, islets of Langerhans, osteocytes, myoblasts, satellite cells, endothelial cells, adipocytes, preadipocytes, biliary epithelial cells, and progenitior cells of any of these cell types.

In some embodiments, the cells used in the methods of the present disclosure may be from any suitable species of animal, for example a mammal, such as a human, canine (e.g. dog), feline (e.g. cat), equine (e.g. horse), porcine, ovine, caprine, or bovine mammal.

The cell composition used to prepare the cryopreservation composition including the at least one glycolipid-containing cell suspension can be combined with the at least one glycolipid in a variety of ways. In some embodiments, a cell composition can be combined with an aqueous liquid medium, such as an aqueous solution, containing the at least one glycolipid. In this regard, the cell composition can be added to the medium containing the at least one glycolipid, the medium containing the at least one glycolipid can be added to the cell composition, or both. For example, a gradual combination, optionally with gentle agitation, can be conducted.

In some embodiments, such as when a previously preserved living cell composition is used to form the cryopreservation composition, if the cell composition is chilled or cooled, it may be thawed (and/or brought to a temperature of about 37° C.) prior or after to combining it with the at least one glycolipid-containing medium. Any suitable thawing/heating technique can be used.

In some embodiments, to achieve the positive effects of exposure of the cells to the at least one glycolipid, the cells to be preserved may be incubated in (or exposed to) the at least one glycolipid-containing medium for at least three hours (it may be possible to achieve the positive effects with shorter periods of incubation/exposure in some embodiments), at any suitable temperature, such as normothermic temperatures (or hypothermic temperatures), i.e., a temperature sufficient to associate the at least one glycolipid with the cell membrane. Depending on the cells to be preserved, such temperatures can include temperatures ranging from room temperature to just over physiological +37° C., room temperature to +40° C. (provided that such exposure does not cause cell death), temperatures ranging +25° C. from to +37° C., temperatures ranging from +25° C. from to +35° C., temperatures ranging from +25° C. to +30° C., temperatures ranging from −5° C. to +20° C., temperatures ranging from −5° C. to +15° C., temperatures ranging from −5° C. to +10° C., temperatures ranging from −5° C. to +5° C., temperatures ranging from 0° C. to +10° C., temperatures ranging from 0° C. to +9° C., temperatures ranging from 0° C. to +8° C., temperatures ranging from 0° C. to +7° C., temperatures ranging from 0° C. to +6° C., temperatures ranging from 0° C. to +5° C., temperatures ranging from 0° C. to +5° C., temperatures ranging from 0° C. to +4° C., temperatures ranging from 0° C. to +3° C., temperatures ranging from 0° C. to +2° C., temperatures ranging from +1° C. to +8° C., temperatures ranging from +1° C. to +6° C., temperatures ranging from +1° C. to +4° C., temperatures ranging from +1° C. to +3° C., temperatures ranging from +2° C. to +9° C., temperatures ranging from +2° C. to +6° C., temperatures ranging from +2° C. to +4° C., temperatures ranging from +3° C. to +8° C., temperatures ranging from +3° C. to +6° C., temperatures ranging from +3° C. to +5° C., temperatures ranging from +4° C. to +8° C., temperatures ranging from +4° C. to +6° C., temperatures ranging from +5° C. to +9° C., temperatures ranging from +5° C. to +7° C., temperatures ranging from +6° C. to +10° C., temperatures ranging from +6° C. to +8° C., temperatures ranging from +7° C. to +9° C., and temperatures ranging from +8° C. to +10° C.

In embodiments, in the methods of the present disclosure the cells to be preserved may be incubated in the at least one glycolipid-containing medium (having one of the above described concentrations of the at least one glycolipid) for at least 6 hours, or for at least 12 hours, or for at least 18 hours, or for at least 24 hours, or for at least 48 hours, or for at least 72 hours. In some embodiments, the cells to be preserved may be incubated for 3 to 120 hours, or be incubated for a longer period of time, such as by incorporation of the at least one glycolipid into the cell culture medium used to maintain the cells. In some embodiments, in the methods of the present disclosure the cells may be incubated in a medium comprising the at least one glycolipid for from 6-72 hours, or from 12-48 hours, or from 18-46 hours, or from 18-36 hours.

In some embodiments, the cells can, for example, be washed with another physiologically-acceptable medium, and then combined with the at least one glycolipid-containing medium.

The combination of the cells with the at least one glycolipid-containing medium can be conducted in any suitable container or vessel.

The prepared cryopreservation composition including at least one glycolipid-containing cell suspension can have any suitable density of the cells. The cryopreservation composition may be then subjected to cooling/storing/warming in any manner conducted in any manner, and may use any additional materials to those described above. For example, in some embodiments, the cryopreservation composition may be used in method for increasing production yield of viable cryopreserved cellular material, comprising: exposure of a cellular material to medium containing at least one glycolipid and a cryoprotectant for a predetermined amount of time to form a cryopreservation composition; subjecting the cryopreservation composition to a preservation protocol comprising cryopreservation at a cryopreservation temperature, such as one of the temperature described infra, e.g., about −80° C. or less, wherein the preservation protocol comprises cooling the cellular material at a cooling rate described infra, such as, for example, greater than about −6.0° C. per minute; and after completion of the preservation protocol, recovering the cryopreserved cellular material: wherein a cell viability (%) of the recovered cryopreserved cellular material is improved (e.g., to the degree/extent discussed above (such as a cell viability (%) of at least 60%) over a preservation protocol under identical conditions except where least one glycolipid is not used, such as where a single cryoprotectant, like DMSO, is used alone as the cryoprotectant, at least 60%. In some embodiments, the recovered cryopreserved cellular material exhibits improved proliferative growth. In some embodiments, the cell viability (%) of the recovered cryopreserved cellular material, is at least one order of magnitude greater than a cell viability (%) achieved by performing a preservation protocol under identical conditions except where least one glycolipid is not used, such as where a single cryoprotectant, like DMSO, is used alone as the cryoprotectant, or is at least two orders of magnitude greater than a cell viability (%) achieved by performing a preservation protocol under identical conditions except least one glycolipid is not used, such as where a single cryoprotectant, like DMSO, is used alone as the cryoprotectant, or is at least three orders of magnitude greater than a cell viability (%) achieved by performing a preservation protocol under identical conditions except where least one glycolipid is not used, such as where a single cryoprotectant, like DMSO, is used alone as the cryoprotectant, or is in a range of one to three orders of magnitude greater than a cell viability (%) achieved by performing a preservation protocol under identical conditions except where least one glycolipid is not used, such as where a single cryoprotectant, like DMSO, is used alone as the cryoprotectant.

Once the cryopreservation composition has been prepared (and the at least one glycolipid has effectively associated with the cells to be preserved), the cooling for cryopreservation may be conducted in any manner, and may use any additional materials to those described above. For example, after adequate exposure to the at least one glycolipid, the cells to be preserved undergo a preservation protocol. This preservation protocol may comprise cooling the cells to be preserved and/or drying the cells to be preserved. For example, the cells may be preserved by freezing, vitrifying, freeze-drying and desiccating. Protocols for preserving cellular material by these techniques are described in the following patents and publications: U.S. Pat. No. 6,395,467 to Fahy et al.; U.S. Pat. No. 6,274,303 to Wowk et al.; U.S. Pat. No. 6,194,137 to Khirabadi et al.; U.S. Pat. No. 6,187,529 to Fahy et al.; U.S. Pat. No. 6,127,177 to Toner et al.; U.S. Pat. No. 5,962,214 to Fahy et al.; U.S. Pat. No. 5,955,448 to Calaco et al.; U.S. Pat. No. 5,827,741 to Beattie et al.; U.S. Pat. No. 5,648,206 to Goodrich et al.; U.S. Pat. No. 5,629,145 to Meryman; U.S. Pat. No. 5,242,792 to Rudolph et al.; and WO 02/32225 A2, which corresponds to U.S. patent application Ser. No. 09/691,197 to Khirabadi et al., the disclosure of which are each hereby incorporated in their entirety by reference.

The cryopreservation portion of the preservation protocol typically involves cooling cells to temperatures well below the freezing point of water, e.g., to about −80° C. or lower, more typically to about −130° C. or lower. Any method of cryopreservation known to practitioners in the art may be used. For example, the cooling (freezing) protocol for cryopreservation may be any suitable type in which the cryopreservation temperature may be lower (i.e., colder) than about −20° C., such as about −80° C. or lower (i.e., colder), or about −135° C. or lower (i.e., colder). In some embodiments, the cryopreservation temperature may be in a range of from about −20° C. to about −200° C., or about −30 to about −175° C., or about −50° C. to about −160° C., or about −65° C. to about −150° C., or about −75° C. to about −135° C., or about −80° C. to about −130° C., or about −90° C. to about −125° C. or about −100° C. to about −115° C.

In some embodiments, the preservation protocol may include continuous rate cooling from the point of ice nucleation to −80° C. or any of the above disclosed cooling temperatures, with the rate of cooling depending on the characteristics of the cells/tissues being frozen. For example, the cooling (freezing) protocol for cryopreservation may be at any suitable rate, such as a rate (and/or average cooling rate, for example from the initial temperature of the sample to the cryopreservation temperature) may be greater than about −0.1° C. per minute, or greater than about −4.0° C. per minute, or greater than about −6.0° C. per minute, or greater than about −8.0° C. per minute, or greater than about −10.0° C. per minute, or greater than about −14.0° C. per minute, or greater than about −25.0° C. per minute. The cooling rate (and/or average cooling rate), such as, for example, for continuous rate cooling (or other types of cooling), may be, for example, from about −0.1° C. to about −10° C. per minute or about −1° C. to about −2° C. per minute. The cooling rate may be about −0.1 to about −9° C. per minute, about −0.1 to about −8° C. per minute, about −0.1 to about −7° C. per minute, about −0.1 to about −6° C. per minute, about −0.1 to about −5° C. per minute, about −0.1 to about −4° C. per minute, about −0.1 to about −3° C. per minute, about −0.1 to about −2° C. per minute, about 0.1 to about −1° C. per minute, about 0.1 to about −0.5° C. per minute, about −1 to about −2° C. per minute, about −1 to about −3° C. per minute, about −1 to about −4° C. per minute, about −1 to about −5° C. per minute, about −1 to about −6° C. per minute, about −1 to about −7° C. per minute, about −1 to about −8° C. per minute, about −1 to about −9° C. per minute, about −1 to about −10° C. per minute, about −2 to about −3° C. per minute, about −2 to about −5° C. per minute, about −2 to about −7° C. per minute, about −2 to about −8° C. per minute, about −2 to about −20° C. per minute, about −4 to about −10° C. per minute, about −4° per minute to about −8° C. per minute, about −4 to about −6° C. per minute, about −6 to about −10° C. per minute, about −6 to about −9° C. per minute, about −6 to about −8° C. per minute, about −6 to about −7° C. per minute, about −7 to about −10° C. per minute, about −7 to about −9° C. per minute, about −7 to about −8° C. per minute, about −8 to about −9° C. per minute, about −9 to about −10° C. per minute, about −7 to about −30° C. per minute, about −10 to about −25° C. per minute, about −15 to about −25° C. per minute, about −20 to about −25° C. per minute, or about −20 to about −30° C. per minute.

Once the cells are cooled to about −40° C. to −80° C. or lower by this continuous rate cooling, they may be transferred to liquid nitrogen or the vapor phase of liquid nitrogen for further cooling to the cryopreservation temperature, which is typically below the glass transition temperature of the freezing solution. The cells may be cooled to about −40° C. to about −75° C., about −45° C. to about −70° C., about −50° C. to about −60° C., about −55° C. to about −60° C., about −70° C. to about −80° C., about −75° C. to about −80° C., about −40° C. to about −45° C., about −40° C. to about −50° C., about −40° C. to about −60° C., about −50° C. to about −70° C., or about −50° C. to about −80° C. before further cooling to the cryopreservation temperature.

The warming protocol may involve a two-step warming procedure (such as that described by Campbell et al., Two stage method for thawing cryopreserved cells; see, for example, U.S. Pat. No. 6,596,531, the disclosure of which is hereby incorporated by reference in its entirety. In the two-step warming protocol, the cryopreserved cells (cryopreserved at the cryopreservation temperature) may be removed from the cryopreservation freezer. The cryopreserved cells are allowed to first slowly warm in a first environment in the first step of the two-step protocol. The environment is not required to undergo any special treatment or have any particular make-up, and any environment may be used. The environment may be a gaseous atmosphere, for example, air. To effect the slow warming of the first stage, the environment may be at a first warming temperature greater than the cryopreservation temperature. The first warming temperature may be near room temperature. For example, temperatures of 30° C. or less, such as about 15° C. to about 30° C., about 20° C. to about 25° C., or about 20° to about 30° C. may be used.

The second step of the two-step warming procedure involves thawing the cells rapidly in a second environment at a second warming temperature that is greater than the warming temperature used in the first warming step. The second warming temperature may be 32° C. or more, about 32° C. to about 50° C., about 35° C. to about 45° C., about 40° C. to about 50° C., about 45° C. to about 50° C., about 32° C. to about 40° C., about 35° C. to about 40° C. or about 37° C. Again, any suitable environment such as gas (air), liquid, or fluid bed may be used as the second environment. For example, a water bath at the warm temperature may be used to effect this rapid thawing.

In embodiments, the cryopreserved cells preserved by the methods of the present disclosure may put to any suitable use, including, for example, research or therapeutic uses. For example, regarding therapeutic uses, the cryopreserved cells may be administered to a human or animal patient to treat or prevent a disease or condition such as degenerative bone disease, osteoarthritis, rheumatoid arthritis, polyarthritis, systemic lupus erythematosus, inflammatory bowel disease, atopy, hepatitis, chronic steroid responsive meningitis-arteritis, beagle pain syndrome, degenerative myelopathy, chronic renal failure disease, dilated and mitral cardiomyopathy, keratoconjunctivitis sicca, immune mediated non-erosive arthritis, immune mediated hemolytic anemia, immune mediated thrombocytopenia, Evans syndrome, intervertebral disc disease, muscle fibrosis secondary to disease or trauma, refractory corneal ulcer, diabetes mellitus, spinal trauma, eosinophilic granuloma complex, hypertrophic cardiomyopathy, cholangitis, spinal injury, exercise induced pulmonary hemorrhage, rhabdomyolysis, corneal ulcer, eczema, multiple sclerosis, muscular dystrophy, spinal injury, diabetes mellitus, hepatitis, myocardial infarction, congestive heart failure, or muscle fibrosis.

The cryopreserved cells can be administered to a patient in any suitable manner. In some embodiments, the cryopreserved cells may be delivered systemically into the bloodstream of a patient, for example by delivery into a vein or artery. In some embodiments, the cryopreserved cells may be delivered topically to the patient (e.g. in the treatment of atopy or other skin disorders). In some embodiments, the cryopreserved cells may be delivered to a local implant site in a patient. Any of these or any combination of these modes of administration may be used in the treatment of a patient.

In some embodiments, a first amount of the at least one glycolipid-containing cryopreserved cells can be delivered systemically into the bloodstream of a patient, and a second amount of the at least one glycolipid-containing cryopreserved cells (e.g. prepared with or separately from the first amount and including the same type(s) or a different type(s) of cells) may be implanted locally in or near one or more skeletal joints in a patient to treat an arthritic condition, e.g. any of those arthritic conditions identified herein. Also, in patient treatments herein, a single administration of the at least one glycolipid-containing cryopreserved cells can be made in some embodiments, while in others multiple separate administrations of the at least one glycolipid-containing cryopreserved cells may be made over time (e.g. weekly or monthly administrations). In further embodiments, the at least one glycolipid-containing cryopreserved cells can be filtered prior to administration to the patient. For example, the at least one glycolipid-containing cryopreserved cells can be passed through an in-line filter positioned in tubing through which the cell suspension is passed into the blood stream of the patient, e.g. into a vein or artery of the patient. Such a filter can, in certain variants, have a particle size cutoff of about 200 micrometers (i.e. exclude from passage particles having a maximum cross-sectional dimension of greater than about 200 micrometers) or lower, or a particle size cutoff of about 170 micrometers or lower, or a particle size cutoff of about 100 micrometers or lower, while allowing the passage of singly suspended cells through the filter.

In some embodiments, provided is an aqueous medium containing the at least one glycolipid useful for preparing a cryopreservation composition including the at least one glycolipid-containing cryopreserved cells. The aqueous medium containing the at least one glycolipid can contain those components, and in amounts, as specified herein. In addition, the aqueous medium containing the at least one glycolipid can be provided in sterile form in a container that is included in a kit. That container may be a vial, bag or other container. In some embodiments, the container may include a "second container" in which the at least one glycolipid-containing cell suspension may be prepared, including for example having an inlet port or other member (e.g. needle septum) and a separate outlet port. Kits disclosed herein may include the container containing the at least one glycolipid-containing aqueous medium along with one or more additional components, for example including a liquid transfer device such as a syringe and attached or attachable needle, and potentially also a container containing a cell composition to be used to prepare the cryopreservation composition comprising the at least one glycolipid-containing cell suspension. The container containing the cell composition can include the composition in a cryopreserved state (e.g. shipped frozen with the kit) or in a non-cryopreserved (e.g. thawed where the cells were previously cryopreserved) state. Kits disclosed herein may also include at least one filter, for example a filter through which a cryopreserved at least one glycolipid-containing cell suspension can be passed prior to administration into a patient, and/or tubing through which the cell suspension can be passed during administration to the patient.

In a first aspect, the present disclosure relates to a method for preserving living cellular material, comprising: exposure of the cellular material to medium containing at least one glycolipid and a cryoprotectant for a predetermined amount of time; and after the exposure, subjecting the cellular material to a preservation protocol comprising cryopreservation at a cryopreservation temperature of about −80° C. or less. In a second aspect the method of the first aspect may be a method in which the at least one glycolipid is an anti-freeze glycolipid. In a third aspect, the method of any of the above aspects may be a method in which the anti-freeze glycolipid is isolated from at least one member selected from the group consisting of plants and insects. In a fourth aspect, the method of any of the above aspects may be a method in which the at least one glycolipid is an anti-freeze glycolipid isolated from one or more member selected from the group consisting of *Tipula trivittat, Ceruchus piceus, Solanum dulcamara, Dendroides canadensis*, and *Cucujus clavipes*. In a fifth aspect, the method of any of the above aspects may be a method in which the at least one glycolipid is a xylomannan-based antifreeze glycolipid. In a sixth aspect, the method of any of the above aspects may be a method in which the at least one glycolipid comprises a β-mannopyranosyl-(1→4) β-xylopyranose backbone and a lipophilic moiety. In a seventh aspect, the method of the sixth aspect may be a method in which wherein the lipophilic moiety is selected from the group consisting of an alkyl chain substituted with one or more hydroxyl groups; an alkyl chain substituted with one or more carboxy groups; a fatty acid; a mono-glyceride; di-glyceride; tri-glyceride; a sterol, and a phospholipid. In an eighth aspect, the method of any of the above aspects may be a method in which the preservation protocol comprises cooling the cellular material from 37° C. to a freezing temperature of the medium at a cooling rate greater than 6° C. per minute. In a ninth aspect, the method of the eighth aspect may be a method in which the preservation protocol comprises cooling the cellular material from 37° C. to a freezing temperature of the medium at a cooling rate in the range of from 10 to 30° C. per minute. In an tenth aspect, the method of any of the above aspects may be a method in which the cellular material is exposed to the medium for at least 3 hours before subjecting the cellular material to the preservation protocol. In an eleventh aspect, the method of any of the above aspects may be a method in which the cellular material is exposed to the medium for 6-72 hours before subjecting the cellular material to the preservation protocol. In an twelfth aspect, the method of any of the above aspects may be a method in which the preservation protocol comprises cooling the cellular material in the medium, where the medium contains at least one glycolipid at a concentration in the range of from 1 pM to 1000 μM. In a thirteenth aspect, the method of any of the above aspects may be a method in which the preservation protocol comprises cooling the cellular material in the medium, where the medium contains at least one glycolipid at a concentration in the range of from 1 pM to 1 nM. In a fourteenth aspect, the method of any of the above aspects may be a method in which the cryoprotectant is selected from the group consisting of acetamide, agarose, alginate, alanine, albumin, ammonium acetate, anti-freeze proteins, butanediol, chondroitin sulfate, chloroform, choline, cyclohexanediols, cyclohexanediones, cyclohexanetriols, dextrans, diethylene glycol, dimethyl acetamide, dimethyl formamide, dimethyl sulfoxide, erythritol, ethanol, ethylene glycol, ethylene glycol monomethyl ether, formamide, glucose, glycerol, glycerophosphate, glyceryl monoacetate, glycine, glycoproteins, hydroxyethyl starch, inositol, lactose, magnesium chloride, magnesium sulfate, maltose, mannitol, mannose, methanol, methoxy propanediol, methyl acetamide, methyl formamide, methyl ureas, methyl glucose, methyl glycerol, phenol, pluronic polyols, polyethylene glycol, polyvinylpyrrolidone, proline, propanediol, pyridine N-oxide, raffinose, ribose, serine, sodium bromide, sodium chloride, sodium iodide, sodium nitrate, sodium nitrite, sodium sulfate, sorbitol, sucrose, trehalose, triethylene glycol, trimethylamine acetate, urea, valine and xylose. In a $15^{th}$ aspect, the method of the $14^{th}$ aspect may be a method in which the medium is a cryoprotectant composition and the cryoprotectant is present in the cryoprotectant composition in an amount of from about 0.05 M to about 11 M. In a $16^{th}$ aspect, the method of the $14^{th}$ aspect may be a method in which the medium is a cryoprotectant composition and the cryoprotectant is present in the cryoprotectant composition at a concentration of less than 1M. In a $17^{th}$ aspect, the method of the $16^{th}$ aspect may be a method in which an additional cryoprotectant including at least one sugar is added to the cryoprotectant composition. In a $18^{th}$ aspect, the method of the $17^{th}$ aspect may be a method in which the additional cryoprotectant is selected from the group consisting of trehalose, glucose, glycerol, maltose, mannitol, mannose, methyl glucose, raffinose, ribose, sucrose, and xylose. In a $19^{th}$ aspect, the method of any of the above aspects may be a method in which the cellular material is selected from the group consisting of organs, cells and tissues. In a 20$^{th}$ aspect, the method of any of the above aspects may be a method in which the cellular material is selected from the group consisting of keratinocytes, hepatocytes, and cardiac myocytes. In a 21$^{th}$ aspect, the method of any of the above aspects may be a method in which the cellular material is selected from the group consisting of mammalian organs, mammalian cells, and mammalian tissues. In a 22$^{nd}$ aspect, the method of any of the above aspects may be a method in which the cellular material is selected from the group consisting of human organs, human cells, and human tissues. In a 23$^{rd}$ aspect, the method of any of the above aspects may be a method in which a cell viability (%) of the cellular material after completion of the preservation protocol is at least 60%. In a 24$^{th}$ aspect, the method of any of the above aspects may be a method in which wherein the medium does not contain an anti-freeze protein/peptide.

The present disclosure relates to Cryopreserved cells obtained by any of the above aspects and/or by exposure of a living cellular material to medium containing at least one glycolipid and a cryoprotectant for a predetermined amount of time; and after the exposure, subjecting the cellular material to a preservation protocol; wherein a cell viability (%) of the cellular material after the preservation protocol is at least 60%. In a further aspect the present disclosure relates to a method comprising administering the cryopreserved cells of claim 25 to a patient.

In a further aspect present disclosure relates to methods for increasing production yield of viable cryopreserved cellular material, comprising: exposure of a cellular material to medium containing at least one glycolipid and a cryoprotectant for a predetermined amount of time to form a cryopreservation composition; subjecting the cryopreservation composition to a preservation protocol comprising cryopreservation at a cryopreservation temperature of about −80° C. or less, wherein the preservation protocol comprises cooling the cellular material at a cooling rate greater than about −6.0° C. per minute; and after completion of the preservation protocol, recovering the cryopreserved cellular material; wherein a cell viability (%) of the recovered cryopreserved cellular material is at least 60%. Here, (i) the recovered cryopreserved cellular material may exhibit improved proliferative growth, (ii) the cell viability (%) of the recovered cryopreserved cellular material is at least two orders of magnitude greater than a cell viability (%) achieved by performing a preservation protocol under identical conditions except where DMSO alone is used as the cryoprotectant, and/or (iii) the cell viability (%) of the recovered cryopreserved cellular material is at least three orders of magnitude greater than a cell viability (%) achieved by performing a preservation protocol under identical conditions except where DMSO alone is used as the cryoprotectant. In these above aspects, the cooling rate is in the range of from about −6 to about −40° C. per minute, or is in the range of from about −6 to about −20° C. per minute or is in the range of from about −6 to about −10° C. per minute. Additionally, (i) the cryoprotectant may be selected from the group consisting of acetamide, agarose, alginate, alanine, albumin, ammonium acetate, anti-freeze proteins, butanediol, chondroitin sulfate, chloroform, choline, cyclohexanediols, cyclohexanediones, cyclohexanetriols, dextrans, diethylene glycol, dimethyl acetamide, dimethyl formamide, dimethyl sulfoxide, erythritol, ethanol, ethylene glycol, ethylene glycol monomethyl ether, formamide, glucose, glycerol, glycerophosphate, glyceryl monoacetate, glycine, glycoproteins, hydroxyethyl starch, inositol, lactose, magnesium chloride, magnesium sulfate, maltose, mannitol, mannose, methanol, methoxy propanediol, methyl acetamide, methyl formamide, methyl ureas, methyl glucose, methyl glycerol, phenol, pluronic polyols, polyethylene glycol, polyvinylpyrrolidone, proline, propanediol, pyridine N-oxide, raffinose, ribose, serine, sodium bromide, sodium chloride, sodium iodide, sodium nitrate, sodium nitrite, sodium sulfate, sorbitol, sucrose, trehalose, triethylene glycol, trimethylamine acetate, urea, valine and xylose; (ii) the cryoprotectant is present in the cryoprotectant composition in an amount of from about 0.05 M to about 11 M. Optionally, the cryoprotectant is present in the cryoprotectant composition at a concentration of less than 1 M. In such aspects, (i) an additional cryoprotectant including at least one sugar is added to the cryoprotectant composition, (ii) the additional cryoprotectant is selected from the group consisting of trehalose, glucose, glycerol, maltose, mannitol, mannose, methyl glucose, raffinose, ribose, sucrose, and xylose (iii) the cellular material is selected from the group consisting of organs, cells and tissues, (iv) the cellular material is selected from the group consisting of keratinocytes, hepatocytes, and cardiac myocytes, (v) the cellular material is selected from the group consisting of mammalian organs, mammalian cells, and mammalian tissues, and/or (vi) the cellular material is selected from the group consisting of human organs, human cells, and human tissues. Furthermore, in such aspects, (i) the cell viability (%) of the recovered cryopreserved cellular material is at least 80%, (ii) the cryopreservation composition does not contain an anti-freeze protein/peptide, (iii) the at least one glycolipid is an anti-freeze glycolipid, (iv) the anti-freeze glycolipid is isolated from at least one member selected from the group consisting of plants and insects, (v) at least one glycolipid is an anti-freeze glycolipid isolated from one or more member selected from the group consisting of *Tipula trivittat*, *Ceruchus piceus*, *Solanum dulcamara*, *Dendroides canadensis*, and *Cucujus clavipes* (vi) the at least one glycolipid is a xylomannan-based antifreeze glycolipid, (vii) the at least one glycolipid comprises a β-mannopyranosyl-(1→4) β-xylopyranose backbone and a lipophilic moiety (the lipophilic moiety may be selected from the group consisting of an alkyl chain substituted with one or more hydroxyl groups; an alkyl chain substituted with one or more carboxy groups; a fatty acid; a mono-glyceride; di-glyceride; tri-glyceride; a sterol, and a phospholipid), and/or (viii) the cell viability (%) is one to three orders of magnitude greater than a cell viability (%) achieved by performing a preservation protocol under identical conditions except where DMSO alone is used as the cryoprotectant.

The foregoing is further illustrated by reference to the following examples, which are presented for purposes of illustration and are not intended to limit the scope of the present disclosure.

EXAMPLES

In the results discussed below, measurement of Cell Viability and Proliferation in FIGS. 1-4 employed AlamarBlue™ by measuring the oxidation/reduction reactions that take place within cells. AlamarBlue™ was added directly to the plates containing cultured cells in culture medium and incubated for 3 hours at 37° C. Upon reduction, AlamarBlue™ changes color and this color change can be measured and quantified. The culture plates were read using a Gemini EM fluorescent microplate reader (Molecular Dynamics) at an excitation wavelength of 544 nm and an emission wavelength of 590 nm.

In addition to measuring viability immediately after rewarming, the ability of the cells to proliferate was also examined using AlamarBlue™. Because AlamarBlue™ is non-toxic, it can be used repeatedly without harming the cells. The cells can be incubated in AlamarBlue™ for 3 hours at 37° C. each day for several consecutive days after rewarming. Once the plate had been read the AlamarBlue™ is removed and the cells incubated overnight in regular cell culture medium until the next day. Increased metabolic activity is indicative of proliferation.

While some cells, for example fibroblasts, are easily cryopreserved other cell types like keratinocytes, hepatocytes, and cardiac myocytes do not freeze well and cell yields are often well below 50%, as shown in FIG. 1 (Cell viability after cryopreservation). Keratinocytes were cryopreserved in vials or in culture plates in 10% DMSO in RPMI. Metabolic activity was measured immediately after thawing and for several days post thaw. Cell viability (in percent of untreated controls) was calculated as the mean (±SEM) of 120 replicates.

To obtain the isolated AFGL, different schemes were used to reduce the presence of protein contaminants. Variations of the purification procedure that were used depended on the species from which the AFGL was being isolated. 1H NMR spectroscopy was used to determine the presence of AFGL and to confirm the absence of antifreeze protein in the ice-purified samples. Methodology for the isolation of the AFGL, from the respective organism (identified below) is known.

The experiments described below were performed using serial dilutions of AFGL in 1.0 M dimethyl sulfoxide (DMSO) and compared with 1.0M DMSO solution alone.

Figure 2:
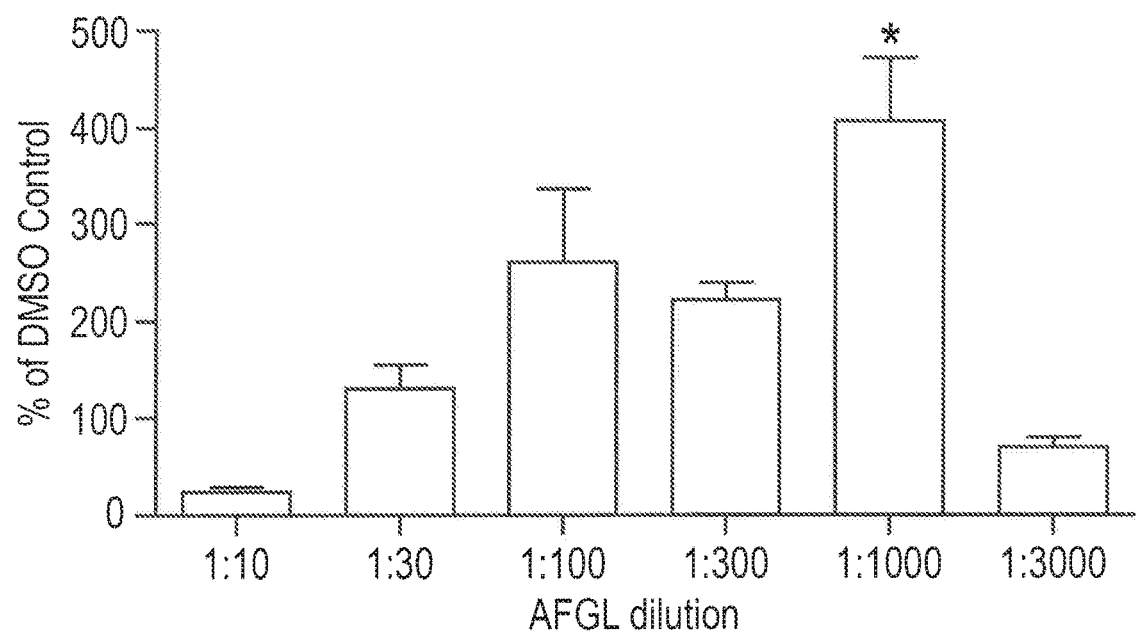
FIG. 2 is an illustration of the data obtained with respect to cell survival after cryopreservation with serial dilutions of *Tipula trivittat* AFGL in DMSO, where cells were exposed to AFGL in 1M DMSO before being cryopreserved.

Briefly, a rat smooth muscle cell line, A10, was plated at 20,000 cells/well in a 96 well tissue culture plate and left overnight in the incubator. The next day, the plate was placed on ice and the cells were treated with 0.5M mannitol before addition of 1.0M DMSO +/−AFGL. Cells were allowed to equilibrate with 1.0M DMSO+/−AFGL for approximately 10 minutes on ice before the plate was cooled at −1.0° C./minute to −80° C. in a controlled-rate freezer that also included a nucleation step at approximately −6.0° C. The plate was stored overnight and thawed the next day. For thawing, the plate was removed from storage (−135° C.) and left at −20° C. for 30 minutes, then it was placed in a water bath at 37° C. and thawed rapidly before being placed on ice. The cryoprotectant solution was diluted using cell culture medium with 0.5M mannitol followed by washes with just cell culture medium. The cells were allowed to recover for 60 minutes in the incubator and then alamarBlue was added at 10% volume and left for 3 hours at 37° C. The plate was read using a fluorescent microplate reader at an excitation wavelength of 544 nm and an emission wavelength of 590 mm. Cell viability was calculated against cells that were cryopreserved in DMSO alone. As can be seen in FIG. 2 below, cell survival was greatly improved in the presence of AFGL at several dilutions with an AFGL dilution of 1:1000 being significant, p<0.05.

FIG. 2 is an illustration of cell survival after cryopreservation with serial dilutions of *Tipula trivittat* AFGL in DMSO. Cells were exposed to AFGL in 1M DMSO before being cryopreserved. After thawing, metabolic activity was measured with alamarBlue. Cell viability (in percent of DMSO control) was calculated as the mean (±SEM) of 5 replicates. *p<0.05.

For the next set of experiments, A10 cells were plated at 20,000 cells/well in a 96 well tissue culture plate and left overnight in the incubator. The next day, the plate was placed on ice and the cells were treated with 0.5M mannitol before being loaded with 1.0M DMSO+/−AFGL at a 1:1000 dilution. The plate was then cooled at −1.0° C./minute to −80° C. in a controlled-rate freezer that also included a nucleation step at approximately −6.0° C. The plate was stored overnight and thawed the next day. For thawing, the plate was removed from storage (−135° C.) and left at −20° C. for 30 minutes then it was placed in a water bath at 37° C. and thawed rapidly before being placed on ice. The cryoprotectant solution was diluted using cell culture medium with 0.5M mannitol then removed followed by washes with just cell culture medium. The cells were allowed to recover for 60 minutes in the incubator and then alamarBlue was added at 10% volume and left for 3 hours at 37° C. The plate was read using a fluorescent microplate reader at an excitation wavelength of 544 nm and an emission wavelength of 590 mm. The cells were washed with phosphate-buffered saline and then left in culture medium overnight. Then for the next several days, the metabolic activity was again assessed with alamarBlue providing an indication of the proliferative potential of the cells after cryopreservation. Cell viability was calculated against cells that were cryopreserved in DMSO alone. As shown in the FIG. 3, the A10 cells cryopreserved in AFGL had better viability than cells cryopreserved in DMSO alone and were able to proliferate on successive days post thaw achieving a plateau on day 2.

Figure 3:
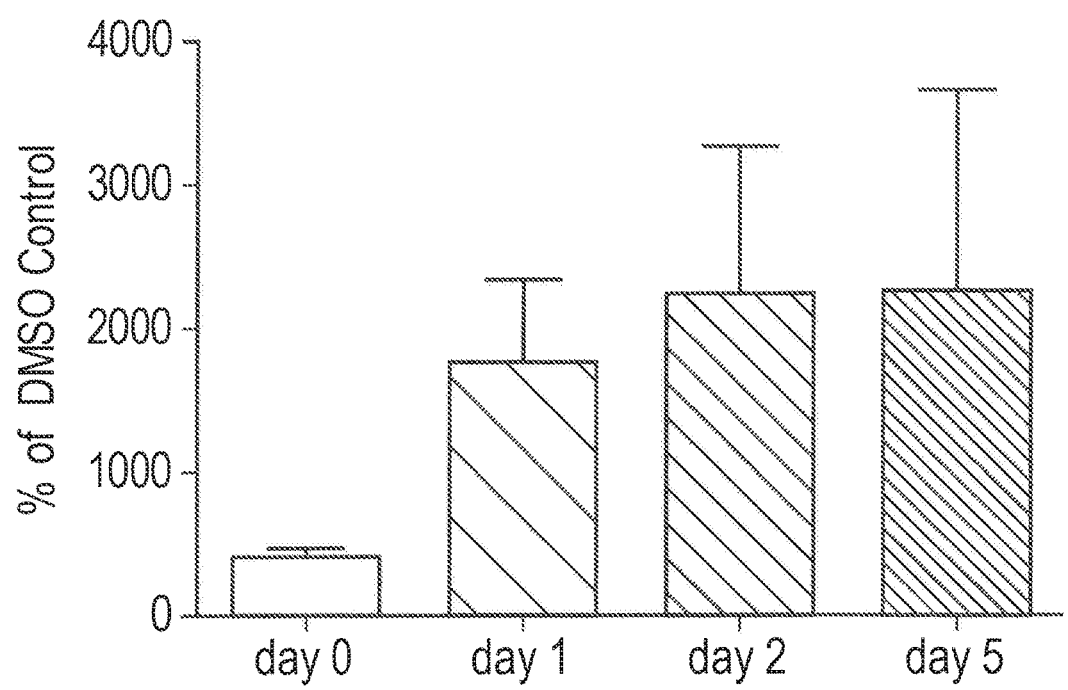
FIG. 3 is an illustration of the data obtained with respect to cell viability and proliferation of A10 cells after cryopreservation, where A10 cells were plated at 20,000 cells/well and then cryopreserved in 1.0M DMSO+/−*Tipula Trivittat* AFGL.

FIG. 3 shows data relating to cell viability and proliferation of A10 cells after cryopreservation. A10 cells were plated at 20,000 cells/well and then cryopreserved in 1.0M DMSO+/−*Tipula Trivittat* AFGL. Metabolic activity was measured using alamarBlue immediately after thawing and for several days post thaw to measure cell proliferation. Cell viability (in percent of DMSO control) was calculated as the mean (±SEM) of 5 replicates.

In the follow set of experiments (similar to those discussed above), serial dilutions of AFGL in 1.0M DMSO from the insects *Tipula trivittat*, and *Ceruchus piceus*, and from the plant *Solanum dulcamara* were used to cryopreserve another smooth muscle cell line, A7R5.

Figure 4:
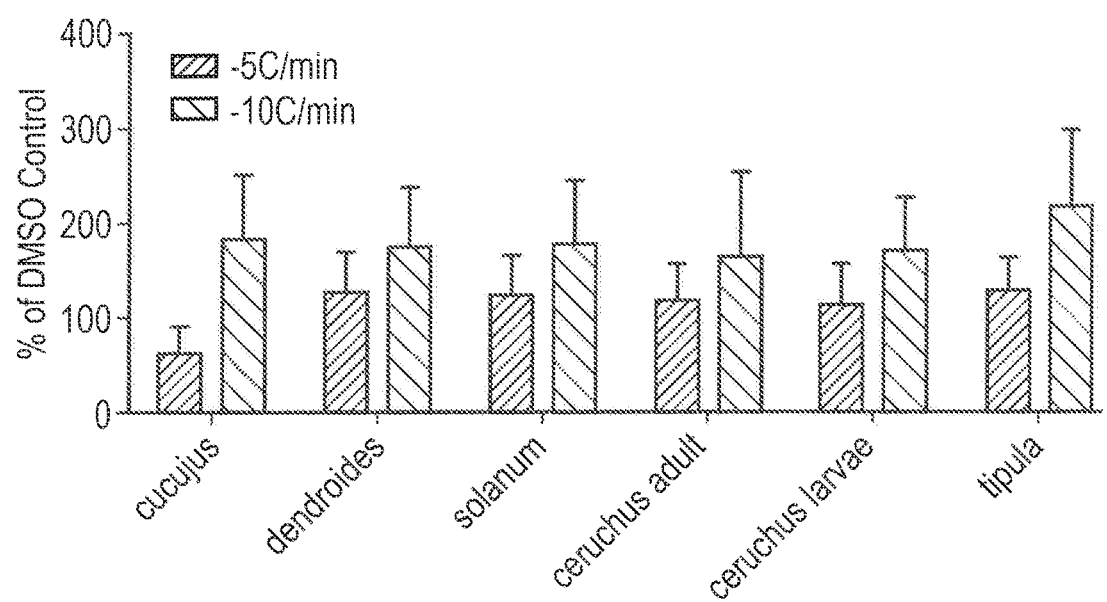
FIG. 4 is an illustration of the data obtained with respect to the cell survival after cryopreservation in DMSO with AFGLs obtained from 4 insect and 1 plant species, where cells were exposed to 10 ppm AFGL in 1M DMSO before being cryopreserved.

Cells cryopreserved in AFGL with DMSO were compared to cells cryopreserved in DMSO alone. As seen in FIG. 4, while the optimal dilution varied, each of the different AFGL glycolipids demonstrated improved cell viability over DMSO alone. FIG. 4 illustrates the data obtained with respect to cell survival after cryopreservation in DMSO with 3 different AFGL glycolipids. Cells were exposed to AFGL in 1M DMSO before being cryopreserved. After thawing, metabolic activity was measured with alamarBlue. Cell viability (in percent of DMSO control) was calculated as the mean (±SEM) of 3 replicates. *p<0.05

In the above experiment, those cells cryopreserved with the AFGL isolated from *Tipula trivittat* showed improved viability at several dilutions.

Further experiments were then performed to evaluate the ability of AFGL glycolipids to improve cell viability under different cooling conditions. Specifically, faster cooling rates were used which usually causes a decrease in viability for most cells types. An endothelial cell line, CPAE, was used in these experiments along with AFGL isolated from *Tipula trivittat, Ceruchus piceus,* and *Solanum dulcamara*. Additionally, three other AFGL, glycolipids were added and included a second AFGL, isolated from the adult of *Ceruchus piceus* as well as AFGL isolated from *Dendroides canadensis*, and *Cucujus clavipes*. Cells were plated at 20,000 cells/well the night before and then cryopreserved the next day as described above in 1.0M DMSO alone or in 1.0M DMSO with each AFGL at 10 ppm dilution. After thawing, viability was assessed using alamarBlue. The results are shown in FIG. 4, which illustrates the cell survival after cryopreservation in DMSO with AFGLs obtained from 4 insect and 1 plant species, where cells were exposed to 10 ppm AFGL in 1M DMSO before being cryopreserved. After thawing, metabolic activity was measured with alamarBlue. Cell viability (in percent of DMSO control) was calculated as the mean (±SEM) of 6 replicates.

As in the above experiments, greater viability was observed when the AFGLs were included with 1.0M DMSO for cryopreservation. The presence of the AFGL generated an improvement even when 100-fold less AFGL was used (compared with, for example, FIGS. 2 and 4, and conditions for cryopreservation were less cell-friendly), Thus, the AFGL had a greater impact on how well the cells survive under suboptimal cooling conditions.

All publications mentioned in the above specification are herein incorporated by reference. Various modifications and variations of the described compositions, methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments.

What is claimed is:

1. A method for preserving living cellular material, comprising:
    exposure of the cellular material to a medium containing at least 0.1 ppm of at least one anti-freeze glycolipid and a cryoprotectant for 6-72 hours, wherein
        the cellular material is selected from the group consisting of keratinocytes, hepatocytes, and cardiac myocytes, and
        the medium is a cryoprotectant composition and the cryoprotectant is present in the cryoprotectant composition in an amount of from 0.05 M to 11 M; and
    after the exposure, subjecting the cellular material to a preservation protocol comprising cooling the cellular material from 37° C. to a sub-zero temperature of the medium at a cooling rate in the range of from 10 to 30° C. per minute, which is followed by cryopreservation at a cryopreservation temperature of about −80° C. or less; wherein
        a cell viability (%) of the cellular material after completion of the preservation protocol is at least 60%.

2. The method of claim 1, wherein the at least one anti-freeze glycolipid is isolated from one or more member selected from the group consisting of *Tipula trivittat, Ceruchus piceus, Solanum dulcamara, Dendroides canadensis*, and *Cucujus* clavipes.

3. The method of claim 1, wherein the at least one anti-freeze glycolipid comprises a β-mannopyranosyl-(1→4) β-xylopyranose backbone and a lipophilic moiety selected from the group consisting of
    an alkyl chain substituted with one or more hydroxyl groups;
    an alkyl chain substituted with one or more carboxy groups;
    a fatty acid;
    a mono-glyceride;
    di-glyceride;
    tri-glyceride;
    a sterol; and
    a phospholipid.

4. The method of claim 1, wherein the medium contains the at least one anti-freeze glycolipid at a concentration in the range of from 1 ppm to 100 ppm.

5. The method of claim 1, wherein, the cryoprotectant is selected from the group consisting of acetamide, agarose, alginate, alanine, albumin, ammonium acetate, anti-freeze proteins, butanediol, chondroitin sulfate, chloroform, choline, cyclohexanediols, cyclohexanediones, cyclohexanetriols, dextrans, diethylene glycol, dimethyl acetamide, dimethyl formamide, dimethyl sulfoxide, erythritol, ethanol, ethylene glycol, ethylene glycol monomethyl ether, formamide, glucose, glycerol, glycerophosphate, glyceryl monoacetate, glycine, glycoproteins, hydroxyethyl starch, inositol, lactose, magnesium chloride, magnesium sulfate, maltose, mannitol, mannose, methanol, methoxy propanediol, methyl acetamide, methyl formamide, methyl ureas, methyl glucose, methyl glycerol, phenol, pluronic polyols, polyethylene glycol, polyvinylpyrrolidone, proline, propanediol, pyridine N-oxide, raffinose, ribose, serine, sodium bromide, sodium chloride, sodium iodide, sodium nitrate, sodium nitrite, sodium sulfate, sorbitol, sucrose, trehalose, triethylene glycol, trimethylamine acetate, urea, valine and xylose.

6. The method of claim 5, wherein an additional cryoprotectant selected from the group consisting of trehalose, glucose, glycerol, maltose, mannitol, mannose, methyl glucose, raffinose, ribose, sucrose, and xylose is added to the cryoprotectant composition.

7. The method of claim 1, wherein the medium does not contain an anti-freeze protein/peptide.

* * * * *